US006368821B1

(12) United States Patent
Greener et al.

(10) Patent No.: US 6,368,821 B1
(45) Date of Patent: Apr. 9, 2002

(54) PROCESS FOR INFECTING EUKARYOTIC CELLS WITH A BACTERIAL VIRUS

(75) Inventors: Alan Lewis Greener, San Diego; Hwai Wen Chang, San Marcos, both of CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 08/834,134

(22) Filed: Apr. 14, 1997

(51) Int. Cl.[7] .......................... C12P 21/00; C12N 15/63; C12N 15/85; C12N 5/10
(52) U.S. Cl. .................. 435/69.1; 435/320.1; 435/69.8; 435/325; 435/358; 435/366; 435/235.1; 435/455; 435/456; 536/23.1; 536/23.7; 536/24.1
(58) Field of Search .............................. 435/69.1, 172.1, 435/172.3, 320.1, 69.8, 325, 358, 366, 235.1, 455, 456; 536/23.1, 23.7, 24.1

(56) References Cited

U.S. PATENT DOCUMENTS 5,128,256 A 7/1992 Huse et al. .................. 435/472

OTHER PUBLICATIONS

Alting–Mees, M et al., "New Lambda and Phagemid Vectors for Prokaryotic and Eukaryotic Expression," *Strategies in molecular biology*, 5:58–61 (1992).
Bannerji, R., "Genetics and Biology of Retroviral Vectors," *Viral Vectors: Gene Therapy and Neuroscience Applications*, pp. 75–88 (Academic Press 1995).
Chalfie, M. et al., "Green Fluorescent Protein aa a Marker for gene Expression," *Science*, 263:802–805 (1994).
Charbit, A. et al., "Permissive Sites and Topology of an Outer Membrane Protein with a Reporter Epitope," *Journal of Bacteriology*, 173:262–275 (1991).
Clément, J. and Hofnung, M., "Gene Sequence of the λ Receptor, an Outer membrane proetin of *E. coli* K12," *Cell*, 27:507–514 (1981).
Gehring, K. et al., "Bacteriophage λ Receptor Site on the *Escherichia coli* K–12 LamB Protein," *Journal of Bacteriology*, 169:2103–2106 (1987).

Greener, A., "*E. coli* SURE™ Strain: Clone 'unclonable' DNA," *Strategies in moleucular biology*, 3:5–9 (1990).
Hopp, T. et al., "A Short Polypeptide Marker Sequence Useful for Recombinant Protein Identification and Purification," *Bio/Technology*, 6:1204–1210 (1988).
Kaneda, Y., "Virus (Sendai Virus Envelopes)–Mediated Gene Transfer," *Cell Biology: A Laboratory Handbook*, pp. 50–57 (Academic Press 1994).
Kuipers, O., "Random Mutagenesis by Using Mixtures of dNTP and dITP in PCR," *Methods in Molecular Biology vol. 57, Chapter 31: In Vitro Mutagenesis Protocols* (Humana Press Inc. 1993).
Lappalainen, K. et al., "Comparison of Cell Proliferation and Toxicity Assays Using Two Cationic Liposomes," *Pharmaceutical Research*, 11:1127–1131 (1994).
Liu, Z. et al., "A Systematic Comparison of Relative Promoter/Enhancer Activities in Mammalian Cell Lines," *Analytical Biochemistry*, 246:150–152 (1997).
Salmons, B. and Günzburg, W., "Targeting of Retroviral Vectors for Gene Therapy," *Human Gene Therapy*, 4:129–141 (1993).
Stevenson, B. et al., "Sequence Organisation and Transcriptional Regulation of the Mouse Elastase II and Trypsin Genes," *Nucleic Acids Research*, 14:8307–8331 (1986).
Stratagene® Instruction Manual, "LipoTAXI™ Mammalian Transfection Kit Instruction Kit: Catalog #204110, Revision #126002" (1996).
Stratagene® Instruction Manual, Mammalian Transfection Kit Instruction Manual: Catalogs #200285, #200385, and #200386, Revision #105001a.
Zhou, Y. et al., "Random Mutagenesis of Gene–sized DNA Molecules by Use of PCR with Taq DNA Polymerase," *Nucleic Acids Research*, 19:6052 (1991).

Primary Examiner—David Guzo
(74) Attorney, Agent, or Firm—Finnegan, Henderson, Farabow, Garrett, & Dunner, L.L.P.

(57) ABSTRACT

Methods are provided for infecting eukaryotic cells with a bacterial virus comprising introducing into the eukaryotic cell DNA that expresses a membrane receptor for a bacterial virus and exposing the cell to the bacterial virus. Eukaryotic cells that contain DNA that expresses a membrane receptor for a bacterial virus are also provided.

16 Claims, 4 Drawing Sheets

PROCESS FOR INFECTING EUKARYOTIC CELLS WITH A BACTERIAL VIRUS

BACKGROUND AND SUMMARY OF THE INVENTION

The ability to exogenously introduce DNA into mammalian cells has become a commonplace and essential part of molecular biology work with many applications. An efficient and reproducible method to accomplish such introduction would be useful, for example, for expressing recombinant proteins, for studying mammalian gene regulation, for functional screening of gene libraries, for creation of transgenic cell lines, and for gene therapy. A number of methods have been used to introduce DNA into mammalian cells.

For example, chemical transfection of cells relies on the treatment of DNA with specific chemicals (e.g., calcium phosphate) or cationic lipids (e.g., lipofectamine). These methods are reasonably reliable although each cell line must be empirically evaluated for optimal efficiency. Also, chemical transfection occasionally suffers from its lack of reproducibility from experiment to experiment and from cell line to cell line. The highest efficiencies are usually achieved with the lipid like compounds. Such compounds, however, often are expensive and many have been demonstrated to be toxic to the cells (1).

A second method to incorporate DNA into mammalian cells is by electroporation. Although this method can be efficient, it is very unreliable and requires a significant amount of handling of the cells. Most cells that become subject to the treatment eventually die during the electric shock, but those that survive have usually taken up the DNA.

A third common technique that exhibits a number of advantages to both transfection and electroporation is infection by virus. Viral infection does not require significant handling of the cells, it is very efficient, high titers of some viruses can be achieved, some viral vector systems have a very large coding capacity, and many cell lines are amenable to this process. However, as attractive as viral systems of gene delivery would appear, significant drawbacks limit or preclude their use. Such drawbacks include cell line specificity, safety concerns, low viral titers, limited vector capacity (in some cases), and cumbersome genomes for genetic manipulations.

The two most commonly used viral vectors are retroviruses and adenoviruses. A primary concern are health and safety issues, particularly for retroviruses. Retroviruses are known causative agents for many types of cancers and infectious diseases. Because their life cycle involves genetic recombination with the host DNA and, because mammalian DNA contain sequences homologous to DNA contained in retroviruses, even vectors that are themselves replication incompetent can be converted to replication competent at a low but measurable frequency. This limits their use in many scientific settings and presents an obstacle to many gene therapy strategies. However, they are utilized in spite of these concerns because they can be propagated at very high titers and libraries can be packaged and infected. Retroviruses only infect actively growing cells and certain cell lines. Another drawback is that the size of foreign DNA that a retroviral vector can incorporate is limited to 5 kb, which may limit its use for many functional genomic cloning strategies.

Adenovirus vectors have a number of advantages over retroviruses. They infect a wide variety of cell lines and, because of their size, can incorporate very large DNA inserts. However, their titers are usually quite low which makes direct library screening difficult to accomplish. In addition, the adenovirus is not benign to either mammalian cells (induction of undesired genes will often occur making certain gene expression studies problematic to evaluate) or people working with the virus, and adverse health effects can result.

Accordingly, there continues to be a need for methods that significantly improve DNA introduction into mammalian cells in any of the areas of efficiency, reproducibility, ubiquity among cell lines and growth phases, and providing for large DNA capacity. It would also be advantageous if one could efficiently introduce primary ligation products (unamplified in another host) so that direct functional cloning is achieved without the need for amplification in E. coli, which is inherently biased. In addition, the ability to target specific tissues or cells by using a wholly benign viral system would be favored by many. This would be particularly advantageous for gene therapy.

An object of the present invention is to provide improved systems for gene delivery. According to certain embodiments, such systems will combine the efficiency and high titers of retroviruses, the cell line ubiquity and large size capability of adenovirus, and the benign effect that chemical transfection (by calcium phosphate) has on the cells.

The present invention provides improved DNA delivery systems by transfecting eukaryotic cells with the membrane receptor for a bacteria virus receptor and infecting these cells with the bacteria virus.

According to certain preferred embodiments, the bacterial virus is an E. coli virus.

According to certain preferred embodiments, the present inventors have achieved improved gene delivery systems by transfecting a mammalian cell line with the membrane receptor for the E. coli bacteriophage lambda and infecting these cells with the E. coli virus.

According to certain preferred embodiments, infection involved the Chinese hamster ovary (CHO) bell line. This infection was specific for cells expressing the receptor with the proper membrane targeting signals and stably transfected cell lines resulted.

According to certain preferred embodiments, cells transfected with DNA encoding a membrane receptor for a bacterial virus are provided. Such cells can be used to express DNA contained in bacterial viruses after infection with the virus.

Exploiting this process would have a number of applications including, but not limited to, basic molecular biology studies and gene therapy strategies. Libraries (both genomic and cDNA) could be directly introduced into mammalian cells without the requirement for bacterial amplification, subcloning, or other such manipulations. Large segments of DNA can be introduced (up to 40 kb for cosmids), and direct expression cloning experiments readily can be performed. By controlling the way that the lambda receptor is expressed, one can conceivably control the cell type or the part of the cell cycle that the DNA enters.

DESCRIPTION OF PREFERRED EMBODIMENTS

The references discussed or cited in this application are incorporated by reference into this application.

The present invention provides advantageous features of all the systems described above. For example, the titer and packaging efficiency of E. coli virus (bacteriophage lambda) DNA is high, its capacity for large inserts can be exploited, it is presumed to be benign to mammalian cells, and it not known to present health concerns for people working with it. In an effort to infect a mammalian cell with E. coli virus, the present inventors transfected a mammalian cell with the receptor gene such that the cell expressed the receptor for lambda on its surface.

Figure 1:
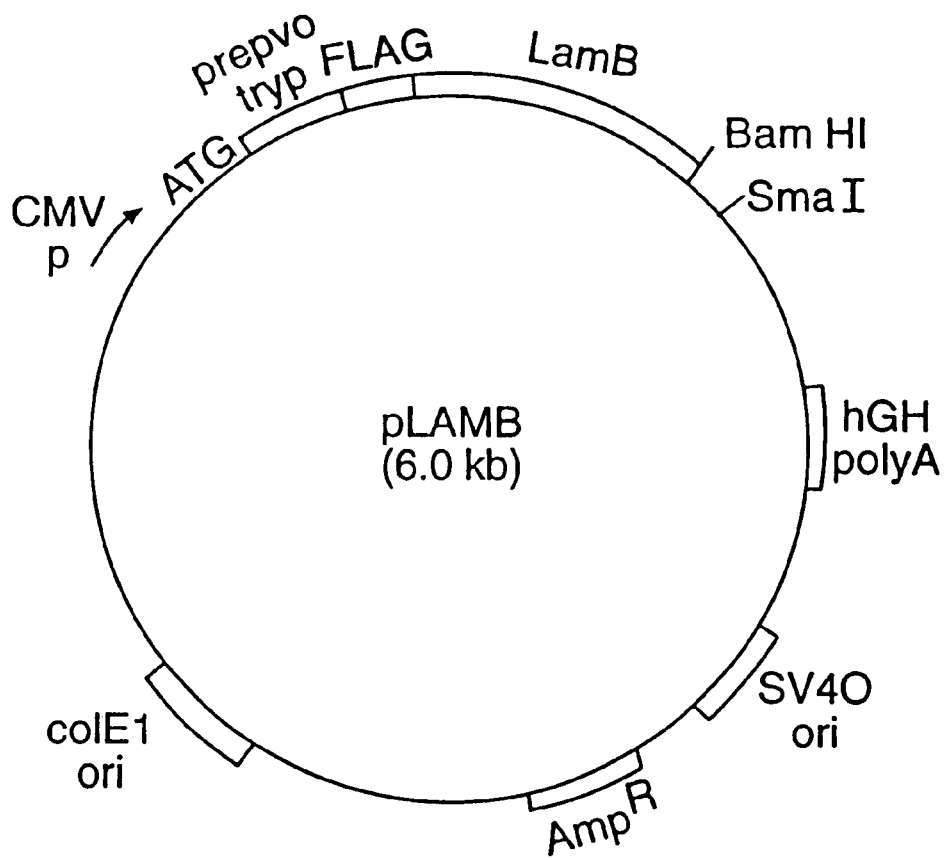
FIG. 1 shows the map of pLAMB.
Figure 2:
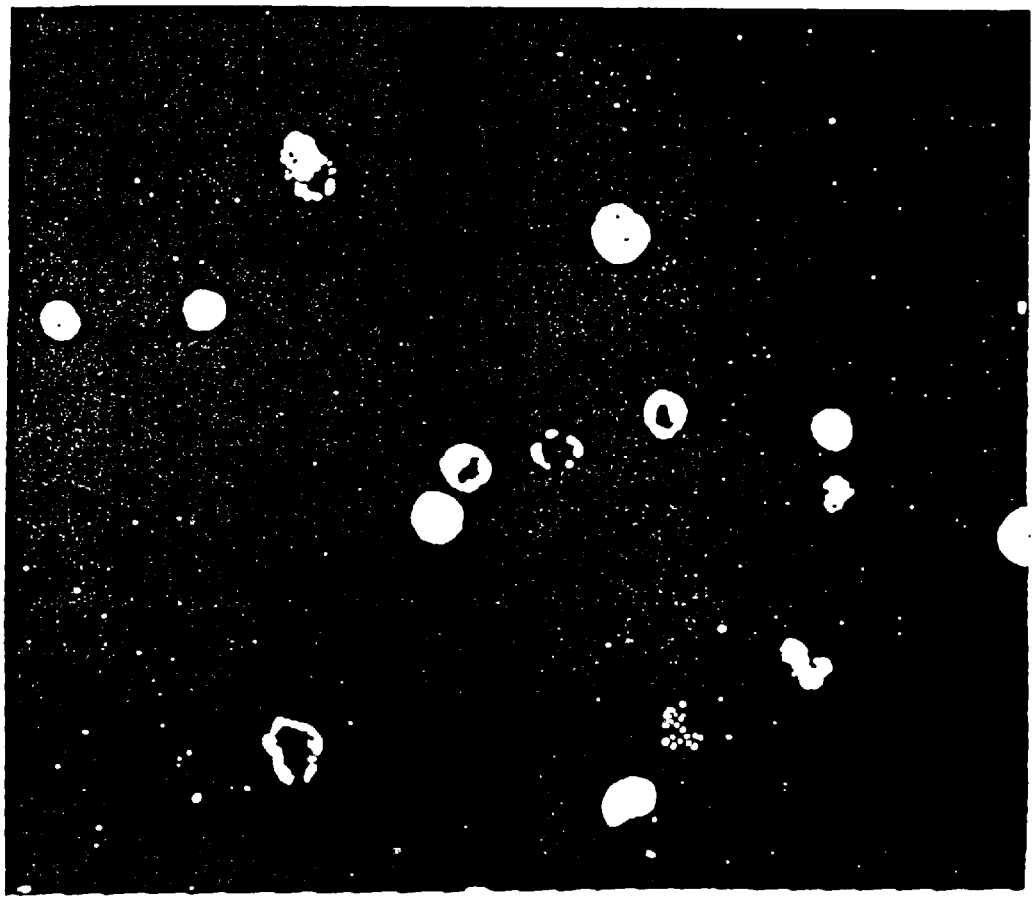
FIG. 2 shows immunofluorescence of CHO cells transfected with pLAMB.

The lambda receptor gene lamB (that also serves as the maltose receptor in E. coli (3)) was cloned into the mammalian expression vector as shown in FIG. 1. In order to direct the receptor to the cell membrane, DNA encoding the E. coli signal peptide sequence at the N-terminus was replaced with DNA encoding a mammalian signal peptide (preprotrypsin (2)). This signal peptide typically is used to export the protein to the cell membrane and typically is cleaved off in this process. The FLAG epitope was also added (5). The plasmid is designated pLAMB and is depicted in FIG. 1. The pLAMB plasmid was then transfected (using lipofectamine) into Chinese Hamster Ovary (CHO) cells and expression/localization monitored with the FLAG epitope (5) that is expressed as a fusion to the N-terminus of the LamB receptor. Immunofluorescence was then performed 48 hours after transfection and the results are presented in FIG. 2.

The present inventors observed that the LamB receptor was localized to the cell membrane although its orientation was not be determined. In fact, a very abundant quantity of the LamB receptor was observed on the surface. When an identical lamB plasmid that contained the wild-type (E. coli) signal peptide rather than the preprotrypsin was transfected in the cells, no membrane florescence was observed.

To evaluate whether lambda virus could infect these transfected cells, a high titer of a lambda virus (ZAP Express Vector; Stratagene) that contains the neo$^R$ gene expressed from the SV40 promoter was added. The neo$^R$ gene can confer in mammalian cells a resistance to G418 (gentamycin (SIGMA)). When $10^9$ phage were added to $10^6$ cells (of which, perhaps, 10% had become transfected with the pLAMB plasmid), G418 resistant colonies (after two weeks) were retrieved. These resistant colonies were not observed if lower titers of phage were used ($10^8$), or if the CHO cells were transfected with the pLAMB plasmid only. These experiments have been repeated on three occasions with identical outcomes.

Direct evidence that the G418 resistant cells (after 2 weeks) were due to the insertion of the lambda DNA into the mammalian cells (or its propagation as an episomal element—an event that is unlikely), genomic DNA from the resistant cells was isolated and subjected to PCR analysis using primers specific for the neo$^R$ gene. The PCR amplification products (for the neo$^R$ gene) were observed for the G418 resistant cells and were not observed for the non-transfected cells.

Since this system was functional in CHO cells, other embodiments will include its application to other commonly used cell lines. Such cell lines include, but are not limited to: NIH 3T3; COS; Mouse L; BHK; ES; and HeLa. The following examples describe methods for determining whether cell lines express transfected lamB, determining whether cell lines are infectible by lambda, optimizing the infection by lambda, producing stable cell lines that express the lambda receptor, and evaluating whether a library of cDNA clones can be screened directly in the mammalian host for a gene of interest. These methods provide a significant improvement in the area of gene transfer, functional genomic cloning, creation of transgenic cell lines, and could have wide application in gene therapy strategies.

These examples are for illustrative purposes and are not intended to limit the scope of the invention.

1. Survey of Cells Lines for Expression of E. coli

To show that the lambda infection observed for CHO cells can occur in other cell lines, the pLAMB expression plasmid (see FIG. 1) will be transfected into the following cell lines: NIH 3T3; COS; Mouse L; BHK; ES; and HeLa.

The pLAMB expression plasmid contains the E. coli gene preceded by a mammalian signal peptide (preprotrypsin (2)). Its expression is directed from the CMV promoter that has been demonstrated to be relatively strong for the cell lines to be tested (4). DNA encoding the FLAG epitope (5) is fused to DNA encoding the N-terminus of the lamB receptor protein to monitor and localize the expression of the protein.

The DNA will be transfected into. each cell line using lipofectamine. After 48 hours, anti-FLAG antibody is used in an immunofluorescence assay to detect the presence and localization of the FLAG epitope. As a negative control, both the untransfected cells and cells transfected with the lamB gene that lacks the mammalian signal peptide will be used.

Our preliminary immunofluorescence data with CHO cells showed that the FLAG epitope was located on the cell surface. However, this did not indicate whether or not the receptor protein is positioned correctly to serve as a receptor for lambda infection. The lamB receptor protein is a 421 amino acid membrane spanning protein that trimerizes in E. coli (3). The fact that lambda was able to infect the CHO transfected cells suggested that the architecture of LamB receptor protein in the mammalian cell was sufficient to serve this function. However, even if the cells listed above express the FLAG epitope (and, hence, the lamB receptor protein) on the surface, the ability to be infected with the lambda should be explicitly tested.

If the cell line of interest does express the FLAG epitope on the cell surface for the lamB-expressing plasmid (and is negative when the signal peptide is absent), the cell line will be tested for its ability to be infected by lambda phage particles. A derivative of ZAP Express Vector will be constructed that contains the green fluorescent protein from Aequorea victoria (6) replacing the neo$^R$ gene. With this construct, the lamB-expressing cells can be assayed two days after infection by fluorescence rather than by the formation of stable G418 resistant cell lines as was done for the CHO cells. This is a more direct assay for the infection of the lambda DNA since nuclear localization and integration (which are typically needed for the formation of stable transfectants) is not required. Although certain preferred embodiments include stably integrated pLAMB plasmids, stable integration is not needed for all embodiments.

If there is little or no localization of the epitope-lamB at the surface or if the lambda phage fails to infect the cell line, the mutagenesis strategy described in Example 4 below will be employed.

2. Creation of lamB—Expressing Stable Cell Lines

In order to evaluate the efficiency of lambda infection, having stable cell lines that express the lamB gene product constitutively is desirable. Therefore, the $hyg^R$ gene (a gene encoding hygromycin resistance) will be inserted at the SmaI site on the pLAMB plasmid discussed above (with the DNA encoding the preprotrypsin signal sequence and the FLAG epitope). This plasmid will then be transfected into all the cell lines that were lambda infectible and selection for $Hyg^R$ cells will be performed.

The stable $Hyg^R$ cells will be treated with anti-FLAG antibody in the immunofluorescence assay to determine the localization and the relative abundance of the lamB-FLAG fusion. If it is detected on the surface, the cells that best express the fusion protein (as determined by immunofluorescence) will be selected and expanded by continued growth on hygromycin. As described below, the cells will be tested by lambda infectibility.

3. Determination of the Efficiency of Lambda Infection

Figure 3:
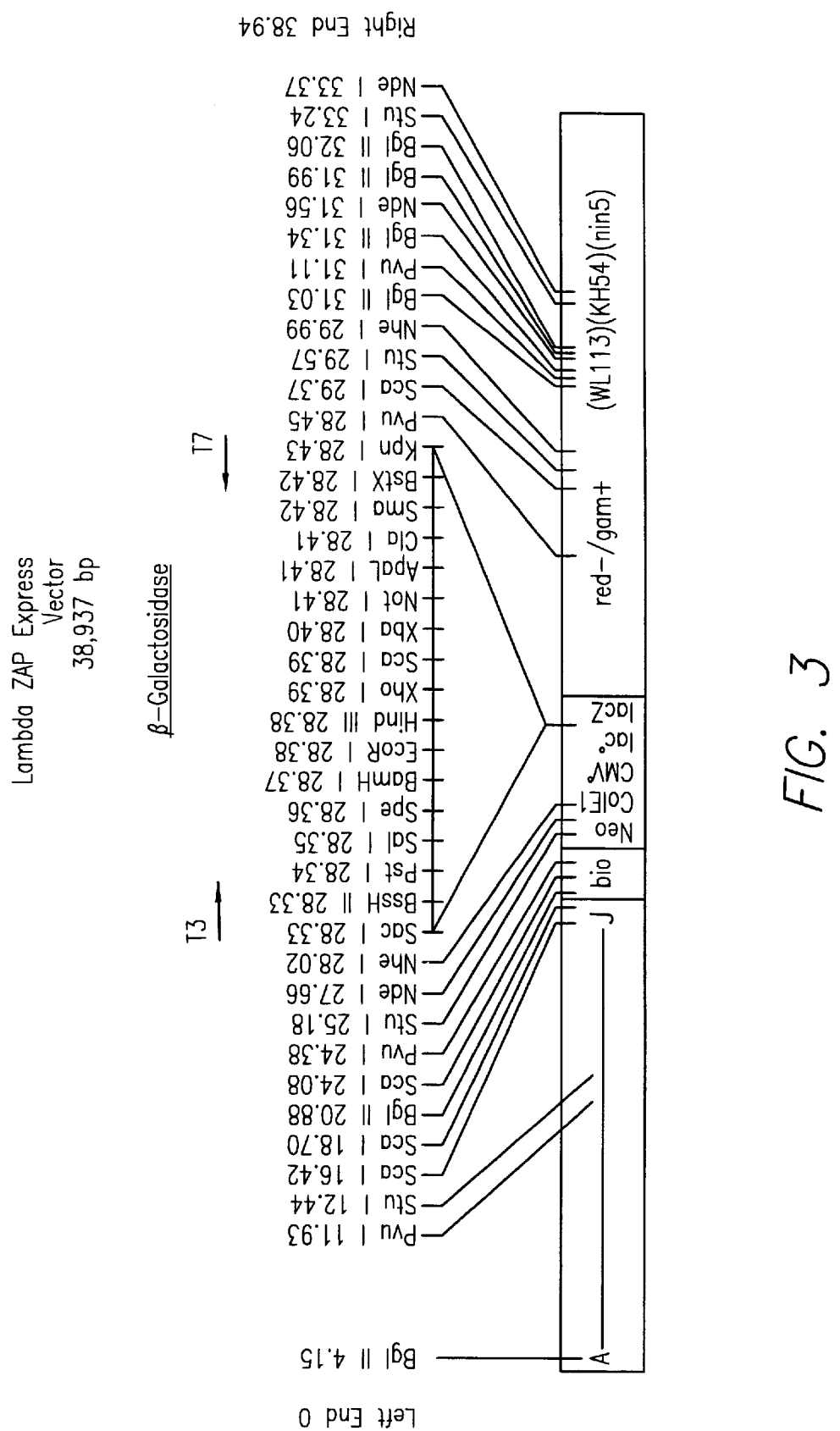
FIG. 3 shows the map of Lambda ZAP Express.
Figure 4:
FIG. 4 shows PCR amplification of genomic DNA with $neo^R$ specific primers. Lane 1: size markers. Lane 2: CHO cells. Lane 3: CHO cells transfected with pBKCMV (neo$^R$ positive control plasmid). Lane 4: stable G418$^R$ CHO cells after lambda infection.

The stable transfectants that express the LamB-FLAG fusion protein will be tested for their ability to be infected by lambda and characterized as to their efficiency. This will be accomplished with the derivative of the lambda ZAP express that contains the green fluorescent protein (GFP) described above (FIG. 3). Since the green fluorescent protein can be readily visualized in a growing cell population within two days after its transfection, it becomes a useful tool to evaluate the efficiency of transfection on a per cell basis. Testing lambda infectivity will be done both on growing and quiescent cells (approximately $10^6$ cells will be used) with a range of phage particles from $10^5$ to $10^9$.

The cells will be monitored by microscopy for fluorescence indicative of the GFP expression 48 hours after addition of the lambda. Counting the number of fluorescent cells compared with those that do not fluoresce will indicate the relative efficiency with which the phage has infected and how many phage provide for maximal efficiency. One demonstrable advantage of a lambda system is the high titer at which the virus can be propagated and purified ($>10^{10}$ phage/ml). Therefore, even in the event that efficient infection is only observed when a large excess of the virus is used, it is not difficult to produce the phage at these levels. The percentage of cells that fluoresce will be determined and the efficiency per lambda phage calculated.

A goal, according to certain embodiments, is to have every cell infected with a single lambda DNA molecule (the possibility and potential utility of multiple infections is discussed below). The number of phage required to yield this result will then serve as the primary "library" number for further experiments. According to certain embodiments, not all cells need to be infected. If all cells do not become infected when a 1000×excess ($10^9$) of lambda is added, mutagenesis to produce a variant lamB plasmid that increases the likelihood of infection will be contemplated (see Example 4 below).

Cell lines that have been stably transfected with the lamB gene and are efficiently infected with lambda will be tested to see whether they are subject to multiple infections (see below). In addition, the relative infectibility between growing and quiescent cells of each type will be compared. If only certain physiological states permit infection for a particular cell line, that will be noted. Mutagenesis and screening of the gene will be considered depending on the relative efficiencies that each cell line and growth condition exhibits. Any inefficiency also will be addressed by attempting certain cell treatments prior to infection if it is believed that such treatments may better expose the receptor protein to the phage particles (see Example 5 below).

If the lambda infection appears efficient, according to certain embodiments, it will be important to determine whether each cell is subject to multiple lambda infections. To address this, the following experiment will be performed. The lamB-expressing stable transfectants (either actively growing or quiescent) will be simultaneously infected with equal numbers of the lambda-GFP phage described above and a second lambda phage that carries a reporter gene which readily can be assayed. For this purpose, one can construct a derivative of ZAP express that contains the entire B-galactosidase (lacZ) gene instead of the truncated alpha complementation segment. The exact number of phage used in this experiment will depend on the efficiency observed above when the cells are successfully infected with one type of lambda phage. In other words, the percentage of cells that are successfully infected with one type of lambda phage will be used to determine the number used for the work with two types of lambda phage. For example, the lower the number of cells successfully used with one type of lambda phage will indicate that a lower number of cells may be used with two types. Forty-eight hours after the dual infection, cells will be assayed for GFP activity and sorted by a standard method (7) to remove GFP-expressing cells from cells that do not express GFP.

The sorted (GFP-expressing) cells will then be stained for B-galactosidase activity by standard methods (8) to determine the percentage of cells that have been multiply infected. Different applications of these systems may be impacted if the cells are susceptible to multiple infections. Different infection strategies may be used depending on these data. For example, this work should show whether the ability to infect with one virus is independent of others or whether the ability to infect with one virus will signify that other viruses can infect simultaneously. This will primarily impact researchers interested in using this system to screen primary libraries. The potential for multiple lambda infections in certain cell lines may have a direct application for a related purpose—the exploitation of this system for a mammalian-based two-hybrid system, which is a method to carry out functional cloning that is best performed by infecting or transfecting two different DNA molecules.

4. Mutagenesis of lamB and Screening for Mutants that Exhibit Greater Infectibility If it appears that one or more commonly used cell lines do not express the LamB adequately (on a quantitative basis), do not permit its membrane localization, or are poorly infected by the virus, a random mutagenesis of lamB will be performed. Mutagenesis may also be used to further improve on any of these properties even if they are satisfactory without such mutagenesis. Random mutagenesis can be performed to test different mutants.

According to certain embodiments of the invention, however, one can use information known from the architecture of the lamB receptor protein within the *E. coli* membrane to specifically target changes on the receptor for use with mammalian cells. For instance, the following are all known: the structure of the lamB receptor protein, its configuration on the *E. coli* membrane, the amino acids that are exposed from the membrane, and the exposed amino acids that are needed for infection of *E. coli*. See, e.g., Gehring K., J. Bacteriology, 169:2103 (1987) and Charbit, A. et al., J. Bacteriology, 173:262 (1991).

One could then determine the structure of the lamB receptor protein in its association with the eukaryotic cell membrane by various methods, including digestion with trypsin, which can be used to determine the amino acids that are exposed. If the exposed amino acids with the eukaryotic cell membrane are different than the exposed amino acids when the protein is associated properly with the *E. coli* membrane, one can modify the protein to obtain a structure having exposed amino acids that are more similar to the structure with the *E. coli* membrane.

Two methods for random mutagenesis will be described as exemplary methods that may be used. The first method will be an in vivo approach using an *E. coli* host strain that is marketed by Stratagene. This strain, XL1-RED, contains mutations in three central DNA repair pathways (9). As a result, the spontaneous mutation rate of DNA propagated in the strain increases 5000–10,000 fold. If the XL1-RED cells carrying the gene of interest are propagated for 30 generations (on a pBluescript copy number vector (Stratagene)), the calculated (and empirically observed) mutation rate results in a single mutation every 1000 base pairs. Therefore, since the lamB coding region is approximately 1 kb, on the average, every plasmid that is recovered after 30 generations of growth should contain 1 mutation in the lamB gene. In addition, some mutations of interest that influence the expression of lamB could fall outside the coding region.

The mutant pools after 30, 60, 90, or further amounts of mutagenic growth will be retrieved by DNA miniprep (standard DNA isolation techniques, including kits sold by Stratagene) and used to transfect the cell line of interest. After 48 hours, the transfected cells will then be infected with a minimal number of lamB-GFP phage. The number will be determined based on the smallest number of phage used in Example 3 above in which infection was detected. If there is an improvement in infection efficiency from Example 3, one can then retrieve these mutants. Forty-eight hours after the lambda infection, the cells will be monitored for GFP fluorescence and sorted to obtain the cells that fluoresce. Once sorted, DNA from the cells will be isolated, the lamB gene amplified by PCR, and cloned back into the expression vector. DNA from positive clones will then be purified and, depending on the number of potential isolates, analyzed individually or pooled. These mutants will then be transfected back into the cells and the process of lambda infection repeated to determine if a quantitative increase in infectibility has been achieved.

Any potential mutants will be sequenced and evaluated in the cell line from which they were isolated. These mutants will also be tested in other cell lines to see if it represents a universal or cell line-specific improvement. The particular location of the mutation may indicate whether the mutant lamB receptor protein is expressed better or altered to improve its accessibility to the incoming lambda virus.

A second method to discover these mutants will be to perform mutagenic PCR (10) on the lamB gene. The mutagenic PCR will be performed using primers that flank the gene and the SV40 promoter which contain the XbaI and BamHI sites that were used for the initial cloning of the gene. Mutagenic PCR conditions include Taq polymerase and elevated concentrations of $Mn^{+2}$. After 40 or 60 rounds of PCR under these conditions, the amplified DNA will be digested with XbaI and BamHI and recloned into the parent plasmid (the plasmid containing the DNA encoding the preprotrypsin signal peptide and the FLAG epitope) digested with the same two enzymes. These DNAs are ligated and transformed into *E. coli* strain SUREΔlamB, a derivative of SURE (11) that does not contain the lamB gene. As a result, this strain is lambda resistant and unable to grow in minimal media with maltose as the carbon source. $Amp^R$ transformants are pooled together and replated on M9 minimal plates with maltose as the carbon source. As shown in FIG. 1, the pLAMB plasmid contains the $Amp^R$ gene. This prescreening removes from the population any plasmid vectors that do not contain inserts, and those that contain mutations that result in a nonfunctional (or truncated) lamB gene.

The cells able to grow on minimal Mal+Amp plates will then be pooled, subject to plasmid DNA miniprep isolation (Qiagen) and this DNA will be the source for transfection into the cell line of interest. The selection/screen for the variants that express better and/or are more easily infected by lambda will proceed as described above with the first method of mutagenesis.

5) Optimization of Lambda Infectibility

It may be useful to optimize the efficiency of lambda infection of particular cell lines that transiently or stably express the lamB (or mutant) transgene. The initial experiments to accomplish this will be to vary the growth conditions/media of the cell line of interest. Our initial data with CHO cells indicated that either quiescent or growing cells could be infected and that the cells did not have to be treated in any special manner. However, the same may not be true for other cell lines. This optimization testing will be performed with limiting amounts of lambda phage for particular cell lines, and these data will be collected for each particular cell line tested. There may be differences for cells that are actively growing compared with stationary cells, as well as differences between cells that express lamB transiently or stably. Some of the experiments that will be performed will include treatment of the cells with compounds that affect the cell's outer membrane. These compounds, such as EDTA, digitonin, and deoxycholate, when used at very low levels, might increase the effective exposure of the lambda receptor.

6) Screening a Lambda Library for a Clone of Interest

The following procedure will be performed to confirm that a complex lambda library may be screened for a unique clone of interest directly in a mammalian cell. As a first example, a "mock" library that contains a readily assayable gene will be screened. This will be performed by taking a ZAP Express premade library of $10^8$ phage and mixing it with 1, 10, 100, 1000 or 10,000 lambda phage that express the Green Fluorescent Protein. The library will also be exposed to a second lambda (ZAP Express containing $neo^R$). Both stably and transiently transfected cell lines will be tested to evaluate at what relative concentration the GFP-lambda is found, and whether these transfectants will also have been infected by the non-selected second lambda (ZAP Express containing $neo^R$), and thus become G418 resistant. The possibility of secondary infection has been explicitly described above. If the lambda-GFP phage can be recovered when present in a minority of the total phage, the system should be amenable for direct library screening. The possibility that more than a single lambda will enter a cell will be exploited for the development of a mammalian 2-hybrid system.

7) Additional Development of the System

The following additional embodiments of the system are contemplated.

(a) Construction of lambda library vectors that permit direct functional cloning of cDNA libraries. These vectors will have the GFP reporter gene (that is expressed from an internal ribosome entry site) or the $G418^R$ ($neo^R$) gene for selection/screening. These vectors will contain promoters to direct high levels of expression of the cloned gene.

(b) To determine possible variants with improved properties, PCR will be used to determine whether all or parts of lambda genome become incorporated in given cell lines. Also, tests will be performed to determine if there are preferred sites of integration.

(c) Inclusion of loxP sites and the cre recombinase gene of phage P1 for the in vivo excision of the cloned gene of interest upon entry into the cell. In addition, the Epstein-Barr virus origin of replication and EBNA-1 gene will be inserted within the loxP sites to permit stable episomal replication in the infected cell line. Work will be performed to improve the stability of the EBV vectors.

(d) Some embodiments will utilize expression of lamB from cell-type specific promoters (instead of the SV40 promoter) in order to target the cell type into which the lambda phage infects.

(e) If multiple lambda infections are possible, vectors will be developed for a mammalian 2-hybrid system for screening for interactive proteins.

(f) Work will be performed to expand the number of cells that lambda will be capable of infecting including cell lines that have historically been difficult to transfect.

(g) Some embodiments will utilize the lambda system in yeast (S. cerevisiae and S. pombe) or in other eukaryotic cells.

(h) The ability to infect mammalian cells with lambda via the lamB gene receptor protein product on the surface shows that one should be able to:

1) Screen primary libraries constructed directly in lambda without having to propagate the DNA in E. coli. This eliminates bias against clones that are toxic to the E. coli.

2) Use a method to introduce DNA directly into cells that have been frozen, then merely thawed and the virus added. This saves many hours/days of tissue culture required to keep cells growing—necessary for retroviral infection, chemical transfection, or electroporation.

3) The success with lambda, may indicate that this system will work for other E. coli viruses, such as P1, that have the capacity to hold twice the amount of foreign DNA, which would expand the utility of the system.

4) This system may be applicable to other organisms, such as yeast, maize, Caenorhabditis, etc., which are model genetic organisms that do not currently have high efficiency gene transfer technology.

5) Transfecting the lambda receptor into stem cells (such as mouse ES cell line) or whole animals to create cell lines or transgenic animals that are infectible by lambda.

6) Inserting the lamB gene that is itself controlled by a specific promoter (for example, a tissue-specific promoter) will permit one to target the cell type of interest that becomes infected by lambda. This has important implications in gene therapy strategies.

7) Because the infection of mammalian cells by lambda might not be "regulatable" as it is in E. coli, more than one virus may be able to enter the cell. This provides a unique opportunity to use any type of functional cloning strategy (such as 2-hybrid) that relies on getting multiple DNA it molecules inside a single cell.

8) Provide a universal method for introducing DNA into mammalian cells. Currently, different cell types often require different methods that have to be determined empirically.

I. LITERATURE CITED

1) Lappalainen et al. (1994) Pharm. Res. 11:1127
2) Stevenson et al. (1986) Nucleic Acid Research 21:8307
3) Clement, J. M. and Hofnung, M. (1981). Cell 27:507
4) Hopp, H. P., Prickett, K. S., Price, V. L., Libby, R. T., March, C. J., Cerretti, D. P., Urdal, D. L. and Conlon, P. J. (1988). Bio/Technology 6:1204
5) Liu, Z., Cashion, L. M., and Twu, J. J. (1997). Anal. Bioch. 246:150.
6) Chalfie, M., et al., (1994). Science 263:802.
7) Current Protocols in Immunology (eds. Coligan, J. E., Kruisbeck, A. M., Margulies, D. H., Sherach, E. M., and Strober, W.) John Wiley and Sons, New York, N.Y.
8) Cell Biology—A Laboratory Handbook (Ed. Julio E. Celis). 1994 Academic Press, NY.
9) Greener, A., Callahan, M., and Jerpseth, B. (1966). In *In Vitro Mutagenesis Protocols* (Ed. Michael K. Trower) Human Press, Totowa, N.J.
10) Zhou, Y., Zang, X., and Ebright, R. (1991). Nucleic Acids Res. 19:6052.
11) Greener, A. (1990). Strategies 3:5.

We claim:

1. The method for infecting a eukaryotic cell with an E. coli lambda virus comprising introducing into the eukaryotic cell DNA comprising DNA encoding a LamB receptor and exposing the cells to the E. coli lambda virus.

2. The method of claim 1, wherein the eukaryotic cell is a mammalian cell.

3. The method of claim 2, wherein the DNA that encodes a LamB receptor further comprises DNA encoding a mammalian signal sequence.

4. The method of claim 3, wherein the DNA encoding the mammalian signal sequence encodes preprotrypsin.

5. The method of claim 1, wherein the eukaryotic cell is a mammalian cell.

6. The method of claim 5, wherein the DNA that encodes the LamB receptor further comprises DNA encoding mammalian signal sequence.

7. The method for expressing DNA in a eukaryotic cell comprising introducing into the eukaryotic cell DNA comprising DNA encoding a LamB receptor, exposing the cell to an E. coli lambda virus that contains the DNA to be expressed, and expressing the DNA in the eukaryotic cell.

8. The method of claim 6, wherein the DNA encoding the mammalian signal sequence encodes preprotrypsin.

9. A eukaryotic cell comprising DNA that encodes a LamB receptor.

10. The eukaryotic cell of claim 9 wherein the cell is a mammalian cell.

11. The eukaryotic cell of claim 9, wherein the DNA that encodes the LamB receptor further comprises DNA encoding a mammalian signal sequence.

12. The eukaryotic cell of claim 11, wherein the DNA encoding the mammalian signal sequence encodes preprotrypsin.

13. The method for incorporating DNA in a eukaryotic cell comprising introducing into the eukaryotic cell DNA comprising DNA encoding a LamB receptor, exposing the cell to an E. coli lambda virus that contains the DNA to be incorporated, and incorporating the DNA in the eukaryotic cell.

14. The method of claim 13, wherein the eukaryotic cell is a mammalian cell.

15. The method of claim 14, wherein the DNA that encodes a LamB receptor further comprises DNA encoding a mammalian signal sequence.

16. The method of claim 15, wherein the DNA encoding the mammalian signal sequence encodes preprotrypsin.

* * * * *